US010495509B2

(12) United States Patent
Bertsch et al.

(10) Patent No.: US 10,495,509 B2
(45) Date of Patent: Dec. 3, 2019

(54) ARRANGEMENT FOR OPTICAL MEASURING OF ONE OR MORE PHYSICAL, CHEMICAL AND/OR BIOLOGICAL, PROCESS VARIABLES OF A MEDIUM

(71) Applicant: Endress + Hauser Conducta Gesellschaft für Mess- und Regeltechnik mbH + Co. KG, Gerlingen (DE)

(72) Inventors: Benjamin Bertsch, Gerlingen (DE); Matthias Grossmann, Vaihingen-Enz (DE); Thilo Kratschmer, Stuttgart (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 291 days.

(21) Appl. No.: 14/106,944

(22) Filed: Dec. 16, 2013

(65) Prior Publication Data
US 2014/0166910 A1    Jun. 19, 2014

(30) Foreign Application Priority Data

Dec. 19, 2012   (DE) .................. 10 2012 112 686
Oct. 11, 2013   (DE) .................. 10 2013 111 235

(51) Int. Cl.
*G01N 21/85*    (2006.01)
*G01J 1/02*    (2006.01)
(Continued)

(52) U.S. Cl.
CPC ........... *G01J 1/0252* (2013.01); *G01J 1/0407* (2013.01); *G01N 21/15* (2013.01); *G01N 21/53* (2013.01);
(Continued)

(58) Field of Classification Search
CPC ............... G01N 21/15; G01N 21/1702; G01N 2021/1704; G01N 2021/1708;
(Continued)

(56) References Cited

U.S. PATENT DOCUMENTS 4,391,129 A  *  7/1983  Trinh ............... G01N 13/02
                                                    250/573
5,179,862 A  *  1/1993  Lynnworth ........ G01F 1/662
                                                    73/861.28
(Continued)

FOREIGN PATENT DOCUMENTS

CN      2472225 Y     1/2002
CN      102004077 A   4/2011
(Continued)

OTHER PUBLICATIONS

German Search Report in corresponding German Application No. 10 2012 112 686.0, dated Jun. 14, 2013.

*Primary Examiner* — Georgia Y Epps
*Assistant Examiner* — Kevin Wyatt
(74) *Attorney, Agent, or Firm* — Mark A. Logan; PatServe

(57) ABSTRACT

An arrangement for measuring process variables of a medium. The arrangement includes a housing embodied for accommodating a measuring apparatus for determining the physical and/or chemical process variable(s), wherein arranged in the housing is at least one window and at least the window contacts the medium, and wherein an oscillatory transducer is provided for transmitting sound waves, characterized in that the window is connected rigidly with the housing, the oscillatory transducer is arranged in a peripheral module having a module housing. The peripheral module is so arranged that the oscillatory transducer transmits the sound waves toward the window, wherein the sound waves pass through the module housing at an exit area, and the peripheral module is so arranged that medium is located in the region of the window and exit area.

16 Claims, 1 Drawing Sheet

(51) Int. Cl.
*G01J 1/04* (2006.01)
*G01N 21/15* (2006.01)
*G01N 21/53* (2006.01)

(52) U.S. Cl.
CPC ... *G01N 21/8507* (2013.01); *G01N 2021/154* (2013.01)

(58) Field of Classification Search
CPC ... G01N 21/53; G01N 21/8507; G01J 1/0252; G01J 1/0407
USPC .......................................................... 250/573
See application file for complete search history.

(56) References Cited

U.S. PATENT DOCUMENTS

| | | | |
|---|---|---|---|
| 5,889,209 A | 3/1999 | Piedrahita et al. | |
| 6,122,970 A * | 9/2000 | Thurn | B06B 1/0651 310/369 |
| 6,426,794 B1 * | 7/2002 | Trainoff | G01N 21/05 356/246 |
| 9,645,080 B2 * | 5/2017 | Matula | G01N 21/53 |
| 2005/0126472 A1 * | 6/2005 | Popescu | B24C 1/045 117/200 |
| 2008/0107151 A1 * | 5/2008 | Khadkikar | G01F 1/696 374/141 |
| 2010/0257940 A1 * | 10/2010 | Berger | G01F 1/662 73/861.27 |
| 2011/0259378 A1 | 10/2011 | Skeidsvoll | |
| 2012/0055262 A1 * | 3/2012 | Sinha | G01F 1/66 73/861.04 |
| 2012/0086938 A1 * | 4/2012 | Folkenberg | G01N 1/4077 356/246 |
| 2012/0255361 A1 * | 10/2012 | Thabeth | B08B 7/028 73/655 |
| 2013/0014592 A1 * | 1/2013 | Mueller | B06B 1/0655 73/861.27 |
| 2013/0235189 A1 * | 9/2013 | Thabeth | B08B 7/028 348/135 |
| 2013/0264142 A1 * | 10/2013 | Kissling | G01F 1/667 181/161 |

FOREIGN PATENT DOCUMENTS

| | | |
|---|---|---|
| CN | 102042965 A | 5/2011 |
| CN | 102105778 A | 6/2011 |
| CN | 201926620 U | 8/2011 |
| CN | 102419304 A | 4/2012 |
| DE | 9015235 U1 | 2/1991 |
| DE | 4317068 A1 | 11/1994 |
| DE | 19811876 A1 | 9/1999 |
| GB | 2212263 A | 7/1989 |
| WO | 2004003506 A2 | 1/2004 |
| WO | WO 2009134145 A1 * 11/2009 | ............... B08B 3/12 |

\* cited by examiner

ARRANGEMENT FOR OPTICAL MEASURING OF ONE OR MORE PHYSICAL, CHEMICAL AND/OR BIOLOGICAL, PROCESS VARIABLES OF A MEDIUM

TECHNICAL FIELD

The invention relates to an arrangement for optical measuring of one or more physical, chemical and/or biological, process variables of a medium. The arrangement includes especially a measuring apparatus, especially a sensor.

BACKGROUND DISCUSSION

A major problem of sensors, which measure in a certain medium, especially liquid, is their fouling. Such fouling is brought about by deposits, biofilms, etc. In the case of almost all sensor types (electrochemical, biochemical, optical, . . . ), such contaminations can lead to wrong measured values and even complete failure of the sensor, wherein, above all, the fouling of membranes, electrodes, active surfaces, optical windows, . . . must be classed as critical.

By way of example, this will be explained based on a turbidity sensor. Fundamentally, the problem arises, however, in the case of all sensors, which measure in liquid and require a certain cleanliness of certain sensor components. Especially to be mentioned here are also similar process variables such as solids content or sludge or slurry level. Measuring devices, which are suitable for determining the corresponding process variables, are manufactured and sold in large variety by the group of firms, Endress+Hauser.

Usually, the sensors are arranged in a sensor housing, and the determining of the process variable happens frequently optically. In such case, electromagnetic waves of a certain wavelength are transmitted from at least one transmitting unit, scattered by the medium to be measured and received by a receiving unit. The measured parameter is deduced as a function of the scattering.

The electromagnetic waves pass through the housing through a material transmissive for the electromagnetic waves, frequently a corresponding window. In the course of time, fouling occurs on the window and the electromagnetic waves can no longer pass through (unimpeded). The measurements become corrupted and the sensor can even fail completely.

In order to maintain the functional ability of the sensor, the window must be cleaned.

The following methods are known for cleaning: Manual, per wiper, with air, by rinsing or washing, and by means of oscillatory or ultrasonic transducers situated in the housing.

In the case of manual cleaning, the sensor must be removed from the process. In case the application involves a pipeline, this requires either that the process must be paused or an expensive retractable assembly used. For hygienic applications, wiper-, air- and rinse or wash cleaning cannot be used, due to dead spaces.

German Patent, DE 43 17 068 C2 shows an ultrasonic transmitter mounted directly on the window. In this way, not only the window, but also the housing, is caused to oscillate. As a rule, the installation space for an ultrasonic transmitter in the sensor is very limited. Because of this, low powered transmitters must be used. Additionally, the energy transmission of the ultrasound into the liquid is not optimal due to the window pane thickness. This leads, in combination with the limited electrical power available in the sensor, to a small cleaning action.

German Patent, DE 90 15 235.2 discloses a turbidity sensor with windows, wherein the windows are kept continuously in oscillation by an oscillatory transducer. As a result of this, highly accurate measurements are not possible.

U.S. Pat. No. 5,889,209 shows an immersible ultrasonic transmitter for a sensor for dissolved oxygen in aqueous media located in relatively open containments such as in a river, in the ocean or in a pond. Ultrasonic transmitter and sensor are located both completely under water and the ultrasonic transmitter transmits, at a small spatial separation of 4 mm to 10 mm from the sensor and a time interval of 5 min to 120 min, ultrasonic waves with a duration of 5 s to 90 s in the direction of the membrane of the sensor. Because of the complete immersion and the water contact, hygienic applications seem out of the question in such case.

German Patent, DE 198 11 876 B4 discloses an oscillation producer, which is coupled mechanically with the window, wherein the window is suspended elastically in the housing. For producing the oscillations, most often, a piezo electrical transducer is used. Large voltages and electrical currents are necessary for its operation. It is clear, thus, that in the immediate vicinity of the measuring system there will be electromagnetic fields, which can lead to EMC problems, especially as regards the measuring electronics. As a rule, the installation space for an ultrasonic transmitter in the sensor is very limited. Because of this, low power transmitters must be used. Additionally, the energy transfer of the ultrasound into the liquid is not optimal due to the window pane thickness. This leads, in combination with the limited electrical power available in the sensor, to a small cleaning action.

SUMMARY OF THE INVENTION

An object of the invention, therefore, is to provide an effective cleaning of the window, while not disturbing the measuring.

The object is achieved by an arrangement including a housing embodied for accommodating a measuring apparatus for determining a physical and/or chemical process variable. Arranged in the housing is at least one window and at least the window contacts the medium. Moreover, an oscillatory transducer is provided for transmitting sound waves. The window is connected rigidly with the housing, the oscillatory transducer arranged in a peripheral module having a module housing, and the peripheral module is so arranged that the oscillatory transducer transmits the sound waves toward the window. Thus, the sound waves pass through the module housing at an exit area, and the peripheral module is so arranged that medium is located in the region of the window and exit area. Thus, the window can be optimally cleaned. The term "window" in the sense of this invention includes an optical window, thus, for instance, in the application in a turbidity sensor, and also a non-optical window, for instance, as applied in a pH-sensor or a conductivity sensor.

In a preferred embodiment, the peripheral module is connected mechanically with the housing. The term "mechanically" includes, in such case, a shape interlocking (by a corresponding arrangement), a force interlocking (by screwing together), or a material bonded interlocking (by adhesive).

For improving the cleaning effectiveness, the sound waves preferably cause cavitation in the medium.

For subsequent mounting, the peripheral module is embodied to plug-on to the housing. Thus, sensors can also be retrofitted.

In an embodiment, the oscillatory transducer is embodied as a piezo electrical transducer. Thus, the sound waves can be produced cost effectively and relatively simply.

In such case, the oscillatory transducer transmits a sound wave frequency of 16 kHz to 200 kHz. This frequency range has been found to be optimal for cleaning.

In an advantageous form of embodiment, the oscillatory transducer is embodied as a radial oscillator, thickness oscillator or shear oscillator. One has, thus, significant freedom in the design of the oscillator, and, thus, of the arrangement.

In a special form of embodiment for increasing amplitude—and, thus, cleaning effectiveness, the oscillatory transducer is embodied as a coupled oscillator.

For optimal coupling, the frequency of the sound wave corresponds to a resonant frequency of the oscillatory transducer.

In a preferred embodiment, a control unit is provided, which operates the oscillatory transducer and the measuring apparatus.

Preferably, the measuring apparatus is a turbidity sensor.

In an advantageous form of embodiment, the housing is embodied to fit in a retractable assembly, especially in a retractable immersion assembly. The arrangement can then be simply and rapidly run into the process.

BRIEF DESCRIPTION OF THE DRAWINGS

The invention will now be explained in greater detail based on the drawing, the figures of which show as follows.

DETAILED DISCUSSION IN CONJUNCTION WITH THE DRAWINGS

Figure 1:
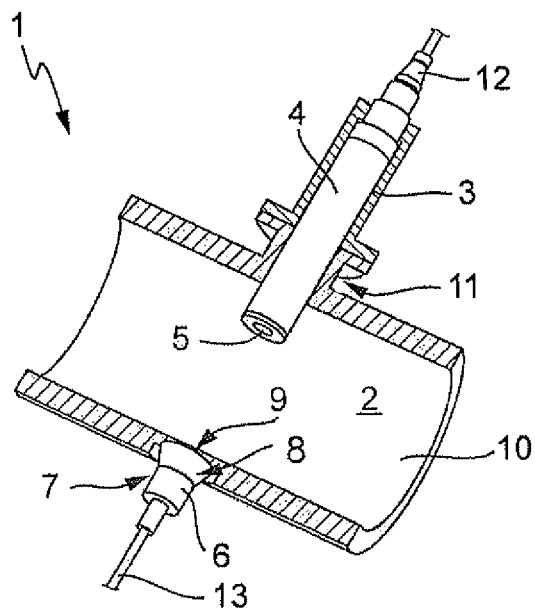
FIG. 1 the arrangement of the invention in a first embodiment in partial cross section.

In the figures, equal features are provided with equal reference characters.

The arrangement of the invention bears in its totality the reference character 1.

In the figures here, the arrangement 1 for measuring medium 2 is embodied in a containment 10. The containment can—such as shown—be a pipe or tube section. The application in a pipe is especially advantageous, since, in such case, the fouling and deposits can be transported away directly by the flow in the pipe. Furthermore, however, application in an (open) pond, channel or the like provide other options. Arrangement 1 can also be used in a retractable assembly, especially a retractable immersion assembly. The medium 2 to be measured is, most often, a liquid, often water for industrial use and waste water. The arrangement also finds application, however, for example in fresh water. Additionally, the arrangement 1 can be applied in non-aqueous media, such as milk, yogurt, . . . , (fruit-)juices or slurries.

Due to the geometry and the forms of embodiment described in the following, the arrangement 1 is also basically suitable for hygienic applications. The arrangement 1 meets established hygiene requirements, such as those prescribed, for instance, by the European Hygienic Engineering and Design Group (EHEDG) or the Food and Drug Administration (FDA).

For measuring at least one physical, chemical and/or biological process variable, the arrangement 1 includes a measuring apparatus 4. Without limitation, the measuring apparatus 4 in the figures is embodied as a turbidity sensor. The measuring apparatus 4 is positioned in a housing 3. Via suitable means, for example, a flange 11, the housing 3 is connected with the containment 10. Via a connection 12, the measuring apparatus 4 is connected with a control unit (not shown). The control unit is, for instance, a measurement transmitter, control station, etc.

The turbidity sensor 4 has at least one light source, frequently an LED, which transmits light in the direction of medium 2. In such case, the term "light" in the sense of this invention is not limited to the visible region of the electromagnetic spectrum, but, instead, includes as electromagnetic radiation any wavelength, especially also in the far ultraviolet (UV) and in the infrared (IR) wavelength ranges.

The light passes through the housing 3 through an optical window 5 transparent for the radiating light coming from the source. Window 5 is, for example, a solid optical window of a hard mineral material, such as, for instance, sapphire. Window 5 and housing 3 are connected rigidly with one another, especially window 5 and housing 3 are connected with one another sealed against intrusion of the medium into the housing.

If the arrangement is used in a non-optical application, the window is obviously embodied as non-optical window. If the arrangement is used, for example, in a pH-sensor, the window is to be understood as a corresponding dividing layer between the medium and the pH-sensitive sensor component. As a further example, in the case of conductivity sensors, the window is to be understood as a region of the housing, in the case of which the magnetic flux, which is produced by the coils, enters into the medium to be measured.

The light is then scattered by the medium. There are different methods for how the scattered light should be registered. Examples include registering at 90° or 135° from the direction of incidence. This is, however, not part of this invention and can be gleaned from established text books.

Used as materials for the arrangement 1, such as the housing 3 and the peripheral module 7, can be stainless steel, synthetic material, such as plastic, or a ceramic. As already mentioned, a turbidity sensor is frequently applied in drinking water, waste water or non-aqueous media. The materials are so selected that they are suitable for the application, for instance, in waste water. Synthetic material must thus be a correspondingly resistant synthetic material, such as PTFE and the like.

Naturally, the window 5 is fouled by the waste water in the course of time. According to the invention, an oscillatory transducer 6 is provided for cleaning the window.

The oscillatory transducer 6 transmits sound waves toward the window 5. The oscillatory transducer 6 is, in such case, embodied as a piezo electrical transducer and transmits sound waves of a certain frequency, which lies in the range between 16 kHz and 200 kHz. The oscillatory transducer 6 thus transmits ultrasound. Preferably, a frequency of 40 kHz is used. Preferably, the transducer transmits at a frequency, which corresponds to the resonant frequency of the piezo electrical transducer. Only a limited power is available for the oscillatory transducer 6. The power of the oscillatory transducer 6 is, for instance, 50 W. The oscillatory transducer 6 is switched on, for instance, every few minutes, for example, every minute or every two minutes, for about 500 ms. This rhythm is selected, since it has been found that the best cleaning effectiveness occurs directly after the oscillatory transducer 6 is switched on.

The oscillatory transducer 6 is arranged in a peripheral module 7. FIG. 1 shows a first embodiment. Ideally, the peripheral module 7 is arranged exactly opposite the window 5. The oscillatory transducer 6 transmits sound waves toward the window 5 and thus cleans it. In order that the sound waves can propagate optimally at the proposed frequency of 16 kHz to 200 kHz, so that the cleaning action is maximum, a separation of the oscillatory transducer 6 from window 5 of about 40 mm to 100 mm is provided. The peripheral module 7 includes a module housing 8; the sound waves pass through the module housing 8 at an exit area 9. In order that the sound waves are optimally coupled in, a "coupling paste", or couplant, is used.

The module housing 8 can also be embodied as a sort of cup, for instance, of stainless steel, which is either integrated in the containment 10 or protrudes through an opening in the containment 10 into the medium 2. Direct contact with the measured medium 2 is, thus, prevented and the arrangement 1 is basically suitable for hygienic applications. For a good transmission of the sound waves, the cup has a thin, constant, wall thickness. Consequently, the peripheral module 7 is more easily reconditionable.

The oscillatory transducer 6 is driven via a connection 13. Control can occur by way of the already mentioned control unit or by a second, additional, unit. The configuration in FIG. 1 is only sensible for tubes with a diameter, which is clearly smaller than the transmission range of the oscillatory transducer 6.

Figure 2:
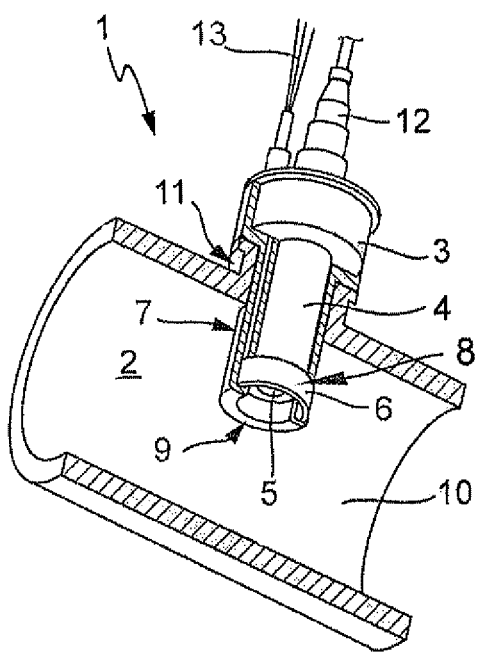
FIG. 2 the arrangement of the invention in a second embodiment in partial cross section.

FIG. 2 shows a second embodiment of the invention. In such case, the peripheral module 7 is located on the housing 3, i.e. module 7 and housing 3 are mechanically coupled. Peripheral module 7 can be embodied as a plug-on module, i.e. such a cleaning system is retrofittable and reconditionable. Module 7 can, however, also be connected with the housing 3 using established methods such as adhesive, screws, rivets etc. Attention should be paid that no medium can get between module 7 and housing 3 and escape from the containment 10. If the arrangement 1 is used in a retractable assembly, the peripheral module 7 can also be mounted on the assembly.

In FIG. 2, the oscillatory transducer 6 is embodied as a radial oscillator and thus surrounds the end of the measuring apparatus 4 facing the medium 2. In this way, the window 5 can be optimally impacted by the sound waves and, thus, cleaned.

Figure 3:
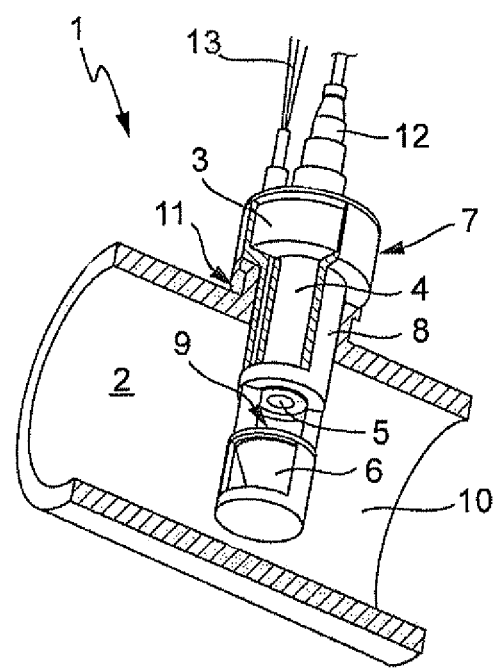
FIG. 3 the arrangement of the invention in a third embodiment in partial cross section.

FIG. 3 shows a third embodiment. In such case, the oscillatory transducer 6 is embodied as a thickness oscillator. The oscillatory transducer 6 is located opposite the window 5, so that the window 5 is optimal struck by the sound waves and cleaned.

The mentioned details as regards the switched-on interval and the separation between oscillatory transducer 6 and window 5 hold analogously for the examples in FIG. 2 and FIG. 3.

The principle underlying the cleaning is cavitation. The oscillatory transducer 6 couples sound waves into the medium 2, whereby waves occur in the medium with positive and negative cyclic pressures. When negative pressure is present at the fouled window 5, a hollow space forms filled with steam. This steam condenses shock like, upon the occurrence of the next positive pressure in the medium, whereby fouling clinging to the window 5 is removed.

The invention claimed is:

1. An arrangement for a measuring apparatus, comprising:
a measuring apparatus embodied to measure a process variable of a liquid medium in a containment, the measuring apparatus including an apparatus housing having a window rigidly connected with the apparatus housing,
wherein the apparatus housing is embodied to connect with the containment,
wherein the apparatus housing is embodied to contact the liquid medium,
wherein the apparatus housing encloses the measuring apparatus and protects the measuring apparatus from the liquid medium, and
wherein the window is disposed to contact the liquid medium;
an oscillatory transducer embodied to generate sound waves in the liquid medium such that the sound waves cause cavitation in the liquid medium; and
a peripheral module including a peripheral module housing,
wherein the peripheral module is structured to hold the oscillatory transducer,
wherein the peripheral module housing is structured to contact the liquid medium,
wherein the peripheral module housing is structured to affix externally to the apparatus housing, and
wherein the peripheral module is affixed externally to the apparatus housing such that the oscillatory transducer is disposed opposite and facing the apparatus housing window and such that the cavitation is directed toward the apparatus housing window.

2. The arrangement as claimed in claim 1, wherein the peripheral module is embodied to plug-on to the apparatus housing.

3. The arrangement as claimed in claim 1, wherein said oscillatory transducer is embodied as a piezo electrical transducer.

4. The arrangement as claimed in claim 1, wherein said oscillatory transducer is configured to transmit a sound wave frequency of 16 kHz to 200 kHz.

5. The arrangement as claimed in claim 1, wherein said oscillatory transducer is embodied as a thickness oscillator or a shear oscillator.

6. The arrangement as claimed in claim 1, wherein said oscillatory transducer is embodied as a coupled oscillator.

7. The arrangement as claimed in claim 1, wherein said oscillatory transducer is configured to transmit sound waves at a frequency corresponding to a resonant frequency of said oscillatory transducer.

8. The arrangement as claimed in claim 1, further comprising:
a control unit configured to operate said oscillatory transducer and said measuring apparatus.

9. The arrangement as claimed in claim 1, wherein said measuring apparatus is a turbidity sensor.

10. The arrangement as claimed in claim 1, wherein said apparatus housing is embodied to fit in a retractable assembly.

11. The arrangement as claimed in claim 1, wherein the retractable assembly is a retractable immersion assembly.

12. The arrangement as claimed in claim 1, wherein the oscillatory transducer is disposed 40 mm to 100 mm from the at least one window.

13. An arrangement for a measuring apparatus, comprising:
a measuring apparatus embodied to measure a process variable of a liquid medium in a containment, the measuring apparatus including an apparatus housing having a window rigidly connected with the apparatus housing, wherein the apparatus housing is embodied to connect with the containment, wherein the apparatus housing is embodied to contact the liquid medium, wherein the apparatus housing encloses the measuring apparatus and protects the measuring apparatus from the liquid medium, and wherein the window is disposed to contact the liquid medium;

an annular oscillatory transducer embodied to generate sound waves radially in the liquid medium such that the sound waves cause cavitation in the liquid medium; and a peripheral module including a peripheral module housing, wherein the peripheral module is structured to hold the oscillatory transducer, wherein the peripheral module housing is structured to contact the liquid medium, wherein the peripheral module housing is structured to affix externally to the apparatus housing, and wherein the peripheral module is affixed externally to the apparatus housing such that the annular oscillatory transducer is disposed around the apparatus housing window and such that the cavitation is directed toward the apparatus housing window.

14. An arrangement for a measuring apparatus, comprising:

a measuring apparatus embodied to measure a process variable of a liquid medium in a containment, the measuring apparatus including an apparatus housing having a window rigidly connected with the apparatus housing, wherein the apparatus housing is embodied to connect with the containment, wherein the apparatus housing is embodied to contact the liquid medium, wherein the apparatus housing encloses the measuring apparatus and protects the measuring apparatus from the liquid medium, and wherein the window is disposed to contact the liquid medium;

an oscillatory transducer embodied to generate sound waves in the liquid medium such that the sound waves cause cavitation in the liquid medium; and a peripheral module including a cup-shaped peripheral module housing, the cup-shaped peripheral module housing having a closed end and an open end, wherein the peripheral module housing is structured to hold the oscillatory transducer at the closed end, wherein the peripheral module housing is structured at the open end to affix externally to the containment, and wherein the peripheral module is affixed externally to the containment such that the oscillatory transducer is disposed externally to the containment and such that the open end of the peripheral module housing is across the containment from the apparatus housing window and is opposite and facing the apparatus housing window such that the cavitation is directed toward the apparatus housing window.

15. The arrangement according to claim 14, wherein the containment is a pipe.

16. The arrangement according to claim 15, wherein the oscillatory transducer is disposed 40 mm to 100 mm from the apparatus housing window.

* * * * *